United States Patent [19]

Winkler

[11] Patent Number: 5,417,208
[45] Date of Patent: May 23, 1995

[54] ELECTRODE-CARRYING CATHETER AND METHOD OF MAKING SAME

[75] Inventor: Josef Winkler, Reading, Pa.

[73] Assignee: Arrow International Investment Corp., Wilmington, Del.

[21] Appl. No.: 135,152

[22] Filed: Oct. 12, 1993

[51] Int. Cl.⁶ .............................................. A61B 5/04
[52] U.S. Cl. ...................... 128/642; 607/98; 607/116; 607/122; 607/280; 604/280
[58] Field of Search ............... 128/642; 607/98, 99, 607/115, 116, 122; 604/280

[56] References Cited

U.S. PATENT DOCUMENTS

| | | | |
|---|---|---|---|
| 3,769,984 | 11/1973 | Muench | 607/122 |
| 3,804,098 | 4/1974 | Friedman | 607/122 |
| 4,259,328 | 7/1988 | Swendson et al. | 607/122 |
| 4,280,511 | 7/1981 | O'Neill | 607/122 |
| 4,630,611 | 12/1986 | King | 128/642 |
| 4,660,571 | 4/1987 | Hess et al. | 607/116 |
| 4,690,155 | 9/1987 | Hess | 128/642 |
| 4,848,352 | 7/1989 | Pohndorf et al. | 128/642 |
| 4,852,580 | 8/1989 | Wood | 128/642 |
| 4,944,088 | 7/1990 | Doan et al. | 128/642 |
| 4,957,110 | 9/1990 | Vogel et al. | 128/642 |

Primary Examiner—Lee S. Cohen
Assistant Examiner—Brian L. Casler
Attorney, Agent, or Firm—Amster, Rothstein & Ebenstein

[57] ABSTRACT

An electrode-carrying catheter has elongate, flexible tubing defining a proximal end, a distal end, and an electrically insulative outer tubular layer intermediate the ends, the tubing including a flexible electrically conductive core of wire and a flexible non-conductive core-covering layer of plastic about the core. At least one electrically conductive ring electrode is crimped on and flush with the outer tubular surface. In order to conduct electrical signals between the proximal end and each of the ring electrodes, a longitudinally-spaced plurality of flexible electrically conductive wires are helically wound around and at least partially into the core-covering layer. The wound wires define a removed section beneath a segment of each of the ring electrodes to enable electrical contact between a respective one of the wound wires and a respective one of the ring electrodes. An electrically conductive flexible flat ribbon is disposed intermediate each of the ring electrodes and the tubing, each ribbon being electrically and physically joined to a respective one of the wound wires and wrapped about the outer tubular surface, each of the ring electrodes being crimped onto a respective one of the ribbons and the outer tubular surface.

15 Claims, 4 Drawing Sheets

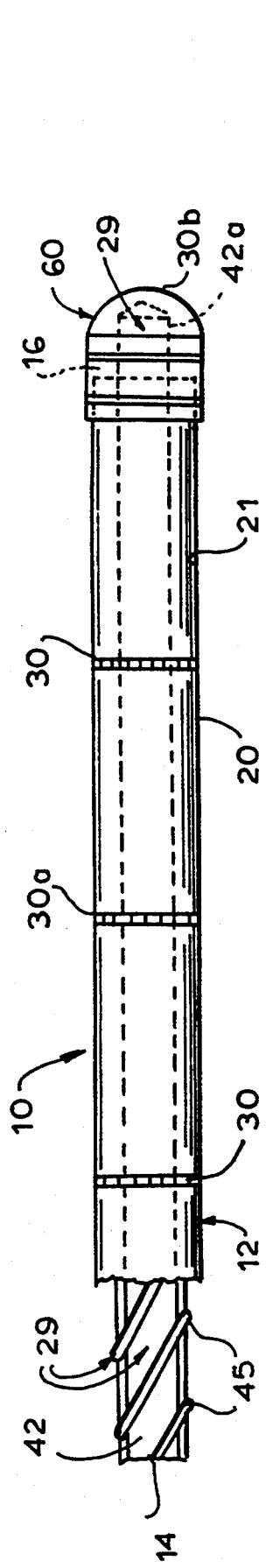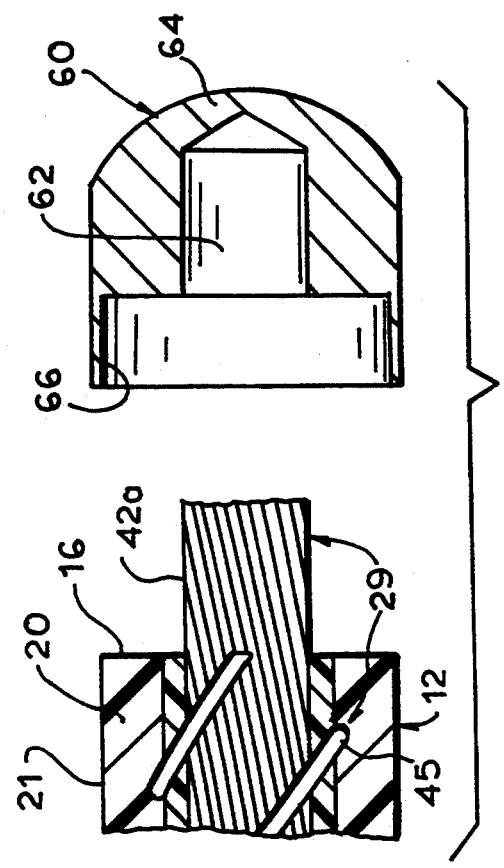

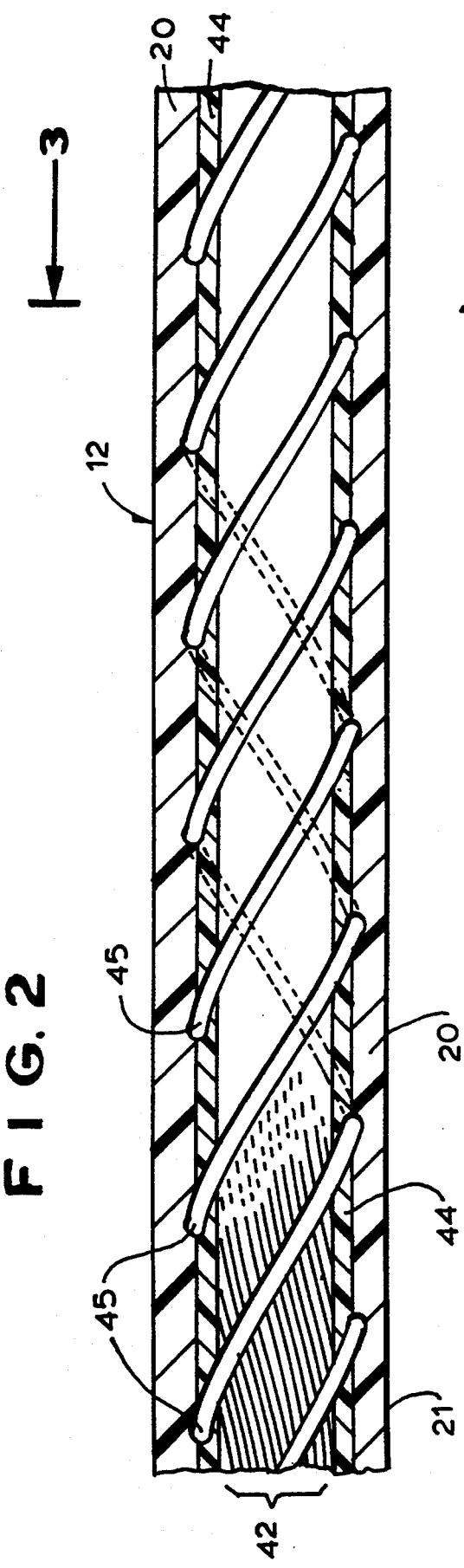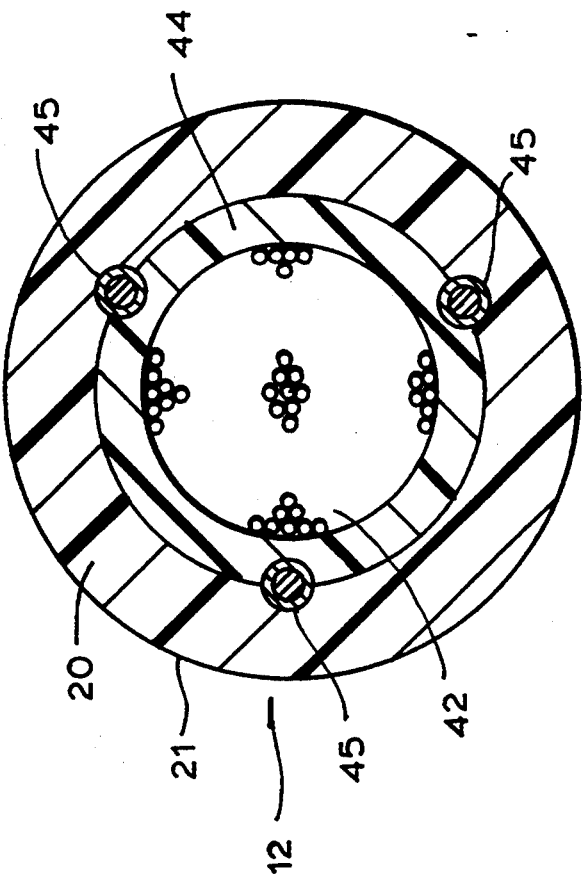

ELECTRODE-CARRYING CATHETER AND METHOD OF MAKING SAME

BACKGROUND OF THE INVENTION

The present invention relates to electrode-carrying catheters, and more particularly to an inexpensive and reliable electrode-carrying catheter and a method of making the same.

Electrode-carrying catheters as well know in the medical art and find diagnostic and therapeutic utility in a wide variety of different applications. For example, mapping catheters are used diagnostically to produce a wave function of the heart's electrical impulses so that a doctor can determine proper functioning or fault, and location of the fault, in the heart. Ablative catheters are used therapeutically to destroy tissue in the heart causing tachycardia, utilizing radio frequency current catheter ablation. Such catheters are also used for heart pacing purposes and for analgesia in various parts of the body. Depending upon the particular application for which the catheter is used, it may be desirable for the catheter to carry one or more side electrodes, one or more end electrodes, or a combination thereof. The use of a plurality of smaller electrodes rather than a single large electrode enables higher current densities to be obtained and frequently enables superior electrical contact with the tissue, both of these being highly desirable factors in connection with ablative catheters in particular, where larger areas of radio frequency ablation in the tissue are desirable.

Electrically conductive wires have never proven to be entirely satisfactory as the electrodes since a functional electrode requires a much larger surface area than can be provided by a flexible wire. Further, unless provisions are made to fix the wire relative to the catheter tubing, it is extremely difficult to ensure that the wire is held in place so as to assure a reliable electrical contact. While a wire could be held in place by use of an electrically conductive adhesive securing the wire to the tubing, it would be extremely difficult to create an electrode by applying an adhesive in a thin layer over a large surface area, as would be necessary to ensure that the electrode layer is flexible.

While a biocompatible conductive paint as an electrode has the advantage of being easily applied in an extremely thin layer to the tubing outer surface by printing techniques, so as to ensure flexibility thereof and cover the wire, there are other problems associated with such conductive paint. While the flexible, thin layer of conductive ink painted on the tubing outer surface forms a good electrical connection with the wire, the conductive paint does not form a reliable physical connection with the typical wire, as necessary to ensure that the passage of the catheter through the human body along the guidewire to the proposed working site does not to some degree remove, separate or abrade away the thin layer of conductive paint.

Typically electrode-carrying catheters are made by applying metal strips on the outer side and/or distal (front) surfaces of a flexible tubing of non-conductive plastic, each side strip acting as a side or ring electrode and each distal strip acting as an end electrode. The presence of the metal strips limits the natural flexibility of the tubing so that the catheter is not of high flexibility throughout its entire length, and this presents problems in threading the catheter into the human body over a guidewire since the diminished flexibility may limit the ability of the catheter to conform to the travel path defined by the guidewire, leading to blood vessel trauma. Nonetheless, such catheters carrying ring electrodes are in favor because of the high level of reliability of the electrical connections therein.

The conventional processes for forming ring or metal band electrodes flush with the outer surface of a catheter are arduous, time-consuming and/or require further processing. For example, in one process, metal bands and sleeves therebetween are slipped over the tubing outer surface with the sleeves maintaining the appropriate spacing between adjacent electrodes; this requires the use of additional pieces (namely, the sleeves) and an arduous assembly process. Another process requires the tubing to be stretched to lower the outer diameter thereof, metal bands placed over the stretched tubing and disposed in appropriate spatial relationship, and the tubing then heated and released. The metal bands sink into the heat-softened tubing outer surface as the tubing resumes its original configuration (except where the metal bands are embedded therein). This technique requires additional stretching, heating and cooling steps.

Accordingly, it is an object of the present invention to provide in one embodiment an electrode-carrying catheter having a ring or metal band electrode thereon flush with the catheter outer surface.

Another object is to provide such a catheter which can mount a large number of electrodes.

A further object is to provide such a catheter wherein there is a reliable adhesive-free electrical contact between an electrode and any conductive wire extending from the proximal end to the electrode, the electrode has a sufficiently large surface area for electrode functioning, and all exposed surfaces are biocompatible.

It is also an object of the present invention to provide such a catheter which is easily and inexpensively manufactured.

It is another object to provide processes for the manufacture of such catheters.

SUMMARY OF THE INVENTION

It has now been found that the above and related objects of the present invention are obtained in an electrode-carrying catheter of low cost and high reliability, comprising elongate flexible tubing defining a proximal end, a distal end, and an electrically insulative outer tubular layer intermediate the ends. The tubing includes a flexible electrically conductive core of wire and a flexible non-conductive core-covering layer of plastic about the core. At least one electrically conductive ring electrode is crimped on and flush with the outer tubular surface. Conducting means are provided for conducting electrical signals between the proximal end and each of the ring electrodes. The conducting means includes, intermediate the core and the outer tubular layer, a longitudinally-spaced plurality of flexible electrically conductive wires helically wound around and at least partially into the core-covering layer and insulated from one another at least by the core-covering layer and from the environment at least by the outer tubular layer. The outer tubular layer and any electrical insulation about the wound wires define a removed section beneath a segment of each of the ring electrodes to enable electrical contact between a respective one of the wound wires and a respective one of the ring electrodes. The conducting means further includes electrically conductive flexible flat means disposed intermediate each of the ring electrodes and the tubing, each of the flat means being electrically and physically joined to a respective one of the wound wires and wrapped about the outer tubular layer. Each of the ring electrodes is crimped onto a respective one of the flat means and the outer tubular layer.

Preferably, the core is a stranded configuration of annealed stainless steel wire having an appreciable torsional strength and a slow return after lateral bending. The core-covering layer and the outer tubular layer are formed of polyurethane. The core-covering layer is softer than the outer tubular layer. The core-covering layer is over-extruded over the core, and the outer tubular layer is over-extruded over the wound wires and the core-covering layer. Where each of the wound wires is covered with electrical insulation, the electrical insulation covering each wound wire defines a removed section beneath one of the electrodes.

Preferably, the flat means is a flat copper ribbon having a pair of opposed ends, the ribbon being electrically and physically joined at one end to a respective one of the wound wires, wrapped under tension completely about the outer tubular layer, and physically joined at the other end to itself. The flat means is preferably joined to the wound wires by welding.

Preferably, the electrodes are platinum with a minor proportion of iridium. Each of the ring electrodes is crimped onto the flat means and the outer tubular layer at at least 24 crimp points. In a preferred embodiment, the ring electrodes crimped onto the flat means and the outer tubular layer are also welded to the flat means, and the outer tubular layer is reformed about the ring electrodes.

Where the core has an extension projecting distally from the distal end, an electrically conductive end electrode is crimped distally onto the core extension and is proximally crimped onto and radially flush with the outer tubular layer.

The present invention also encompasses a process for manufacturing an electrode-carrying catheter of high reliability, comprising the step of over-extruding a soft outer layer of plastic over a flexible, electrically conductive, elongate core of wire. A spaced apart plurality of flexible, electrically conductive wires is helically wound about and at least partially into the soft outer layer. A flexible, non-conducting hard outer layer of plastic is over-extruded over the wound wires and the soft outer layer. Portions of the hard outer layer, and any insulation about the wound wires, are removed at a plurality of spaced locations so as to expose a portion of each of the wound wires. The removed portions at each location are replaced with an electrically conductive flexible ribbon electrically and physically joined to a respective one of the wound wires and wound about the wound wires and hard outer layer. An electrically conductive ring electrode is crimped onto each of the ribbons and the hard outer layer thereabout at each spaced location, flush with the hard outer layer, the ribbons conducting electrical signals between a respective one of the exposed wire portions and a respective one of the ring electrodes.

BRIEF DESCRIPTION OF THE DRAWING

The above and related objects, features, and advantages of the present invention will be more fully understood by reference to the following detailed description of the presently preferred, albeit illustrative, embodiments of the present invention when taken in conjunction with the accompanying drawing wherein:

FIG. 1 is a fragmentary side elevational view of an electrode-bearing catheter according to a preferred embodiment of the present invention, with three side electrodes and one end electrode;

FIG. 2 is a fragmentary side elevational view of the tubing and wound wires thereof, to a slightly enlarged scale;

FIG. 3 is a fragmentary sectional view taken along the line 3—3 of FIG. 2, to a greatly enlarged scale;

FIG. 8 is a fragmentary exploded side elevational view of the catheter and end electrode assembly; and FIG. 9 is a side elevational view of the assembly of FIG. 8 after crimping, with the crimps being greatly exaggerated for expository purposes.

DETAILED DESCRIPTION OF THE PREFERRED EMBODIMENTS

Figure 4B:
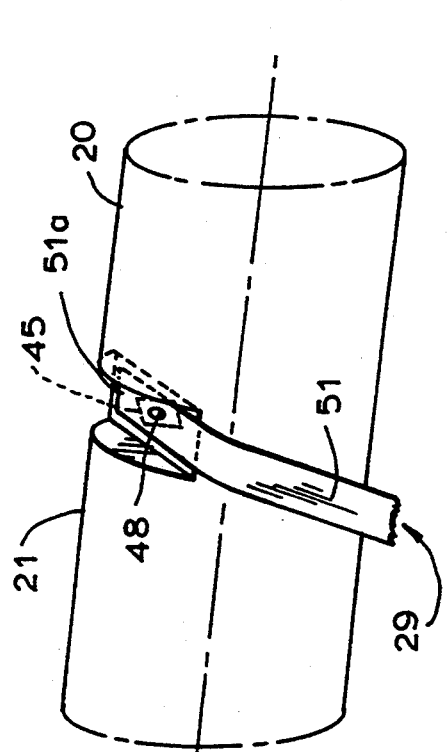
FIGS. 4A–4D are schematics illustrating the process of applying the flat ribbon to the tubing.

Referring now to FIG. 1, therein illustrated is an electrode-carrying catheter according to the present invention, generally designated by the reference numeral 10. While the configuration and dimensions of the catheter will vary with the intended application for the catheter, it is generally of the same overall width and length of the known catheters for the same application. The catheter 10 is formed of elongate, flexible tubing generally designated 12. The tubing 12 defines a proximal end 14, a distal end 16, and a sidewall or outer tubular layer 20 connecting the ends 14, 16 and having an electrically insulative outer surface 21.

Referring now to FIGS. 2–4 as well, at least one electrode 30 is disposed on the tubing 12. The electrode may be a side electrode 30a disposed on the outer surface 21 (three side electrodes being illustrated in FIG. 1), an end electrode 30b disposed on the distal or front end 16 (one end electrode being illustrated in FIG. 1), or a combination thereof. Particular ring electrodes 30a may extend predominantly axially or transversely (i.e., circumferentially) relative to the tubing axis as preferred for a given application. Preferably the side electrode 30a extends fully around the circumference of the tubing 12, and the end electrode 30b extends over the full diameter of the distal end 16 (as illustrated). Conducting means, generally designated 29, are provided for conducting electrical signals between the proximal end 14 and each of the electrodes 30a, 30a, 30a, 30b.

Referring now to FIGS. 2 and 3, the tubing 12 is composed initially of a flexible, conductive core 42 and a flexible, insulating, soft, core-covering layer 44 disposed over the outer surface of the core 42. The soft or core-covering layer 44 may be formed by over-extruding (or otherwise forming) a soft plastic over the wire core 42, the soft layer being relatively softer than the wire core. The core 42 is preferably formed of a wire exhibiting an appreciable degree of torsional stiffness (so that rotation of the proximal end 14 of the tubing is transmitted to the distal end 16) and a slow return or recovery after a lateral bending (so that the catheter makes good contact along its length with the walls of the vessel into which it is inserted). A preferred core 42 is a 0.032 inch outer diameter length of a stranded and twisted configuration of annealed wire, such as 304 stainless steel 7×19. (The annealing process involves heating the stainless steel wire—e.g., to 2,000° F.—so that it becomes formable and tends to retain a configuration into which it is flexed without immediately springing back.) A preferred soft core-covering layer 44 is formed of a soft plastic such as polyurethane having a durometer hardness of 80A available under the trade name Tecoflex (from Thermedics Inc. of Woburn, Mass.).

As part of the conducting means, flexible, insulated, electrically conductive wires 45 (three wires 45a, 45b, 45c being shown, one for each side electrode 30a) are helically or spirally wound around and at least partially into the soft core-covering layer 44 about the core 42. The wound wires 45 are longitudinally spaced apart such that each of the wires 45 is insulated from the two adjacent wires 45 by portions of the soft layer 44 as well as the wire insulation. In order to preclude accidental movement of the spaced apart plurality of wound wires 45 prior to over-extrusion of a hard layer 20 thereover, the wires 45 are helically or spirally wound around the soft layer 44 (under roughly hand tension) so that they at least partially embed themselves within the soft layer 44 (preferably at least 75% of the diameter becoming embedded). The wound wires 45 are preferably insulated magnet wires having a gauge of 34. As the soft layer 44 ensures electrical separation between the various wires 45, the wires are not insulated in order to prevent shorting if they come into contact, but merely to facilitate subsequent processing steps. Indeed, uninsulated wires may used if desired. It will be appreciated that, while only three wires 45 have been illustrated, the number of wires 45 can be varied as desired for particular applications depending on the number of side electrodes 30a. Each wire may be of a different color.

Finally, a flexible, thin insulating layer of plastic is over-extruded (or otherwise formed) over the soft core-covering layer 44 and any exposed portion of wound wires 45 to form the hard outer layer 20 of the tubing 12 defining outer surface 21. The hard layer 20 may be formed of polyurethane or any of the other flexible, but hard, electrically insulative plastics commonly used in catheter construction such as polyvinyl chlorides, polyesters and various copolymers. The hard layer 20 is preferably formed of polyurethane having a durometer hardness of 71D available under the trade name Tecothane (from Thermedics Inc.). Thus the conductive wires 45 are isolated from one other and the environment by means of the core 42, the soft layer 44, and the hard layer 20 as well as any insulation thereon.

The hard layer 20 is preferably over-extruded to a thickness slightly greater than that ultimately desired so that it may be subsequently ground down (preferably using a conventional centerless grinding machine) down to a constant outer diameter, thereby masking irregularities originally present due to the presence of the wires 45 wound on the soft layer 44.

If the soft core-covering layer 44 is of sufficient thickness to receive and electrically isolate the wound wires 45 (which must then be totally embedded therein) and is furthermore subsequently treatable (e.g., curable or modifiable) to provide an abrasion-resistant surface, application of the hard layer 20 may be dispensed with entirely and the soft layer 44, thus treated after the wires 45 are totally embedded therein, will also serve as the hard layer 20.

Figure 4D:
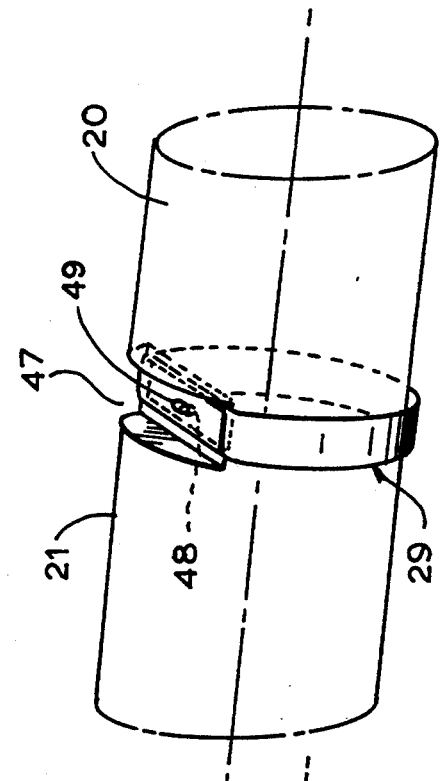
Figure 4A:
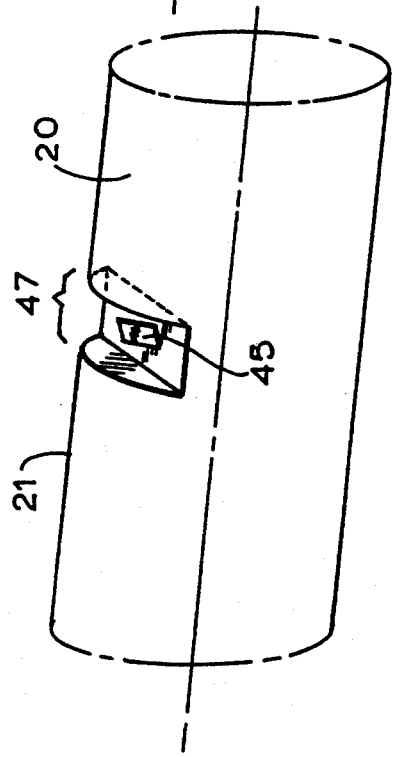

Referring now to FIG. 4A, next, the hard layer 20 of the tubing 12 is removed at a plurality of spaced locations along its circumferential sidewall 21 (corresponding to the ultimate locations of the side electrodes 30a) so as to form windows 47. Each window 47 exposes a portion of a respective one of the wound wires 45 at its respective location. The hard layer 20 can be removed at the desired locations by various techniques such as cutting, skiving, drilling or grinding, but grinding or cutting is preferred as they are easy, quick and precise operations. The windows are preferably formed using a grinding wheel having a diameter suitable for forming windows of the desired size (such as a 0.020 inch diameter) until the grinding has removed a suitable amount of the hard layer 20 and, where present, the insulation about the wire 45, so as to expose the conductive element of the wire 45.

Referring now to FIG. 8, in a similar fashion the hard layer 20 at the distal end 16 of the tubing 12 is removed (e.g., ground by a grinding wheel) in order to remove from the distal end 16 the hard outer layer 20 and, where present, the insulation about the end of the core 42. Grinding of the distal end 16 continues until there is exposed an appropriate length (about 0.035 inch) of the conductive element of the core wire 42, this exposed conductive element projecting forwardly from the distal end 16 of the tubing 12 as a core extension 42a.

It will also be appreciated that the hard layer 20 of the sidewall 21 may have the portions at the particular locations removed therefrom simultaneously to form windows 47. The locations at which the hard layer 20 is to be removed are predetermined by the desired location of the electrodes 30a. Before removal of the portions of the hard layer 20, the wound wires 45 are already in place and in fixed spatial disposition relative to one another. Accordingly, once the location of one wire 45 is determined (perhaps by inspection of the distal end 16 where they are initially visible), then the location of all of the remaining wires 45 is known. Thus, grinding elements of a grinding machine, for example, can be appropriately positioned relative to the known wire, and the desired portions of the hard layer 20 (and, when present, the wire insulation) simultaneously removed at each location. This enables the windows 47 to be inexpensively formed in a low labor operation.

Figure 4C:
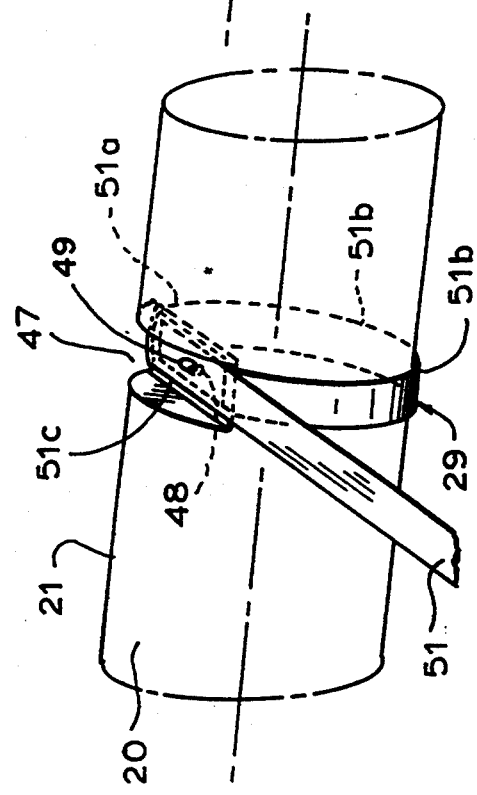

Referring again to FIG. 4B, after creation of the windows 47, a flat conductive element 51, such as a flat copper ribbon (0.001×0.012 inch), is electrically and physically joined to the exposed portion of the wire 45 under the window 47. Preferably the ribbon 51 is welded to the exposed wire 45 at point 48 using a welder such as that available under the trade name Light Force Welder (from Unitek Equipment Inc. of Monrovia, Calif.). Typically, a free ribbon end 51a is first welded to the wire 45. Referring now to FIG. 4C, the ribbon 51 and the tubing 10 are then rotated relative to one another until a shank 51b of the ribbon 51 is wrapped completely one turn (360°) about the hard layer 20, and back on itself. This may be accomplished by rotating the tubing 12 while using a machine to maintain hand tension on the ribbon 51. Next, the as yet unwelded ribbon end 51c of the loop thus formed is welded to the ribbon 51 at point 49 (preferably at the already welded ribbon end 51a). Finally, as seen in FIG. 4D, the ribbon 51 is removed from the ribbon spool (not shown), e.g., by simply applying a quick tug to the ribbon.

While there is an overlap of the ribbon 51c upon itself 51a, the extra thickness of the additional ribbon layer is of no consequence since the ribbon is so thin relative to the depth of the window 47. It will be appreciated that the ribbon performs the role of bringing the signal from the exposed wire (which is located below the hard layer 20) up to the top of the hard layer 20 where it can be fed to an electrode 30a. Preferably the welding equipment uses the electrodes available under the trade name Unitip 111L (available from Unitek Equipment Inc.) or a similar microelectrode which permits the welding equipment to resistively weld the exposed wire 45 and the ribbon 51 together within the confines of window 47.

The application of the ribbon 51 to a wire 45 is then repeated for each of the remaining windows 47, and the tubing 12 is then ready for application of the ring or metal electrodes 30.

Figure 5:
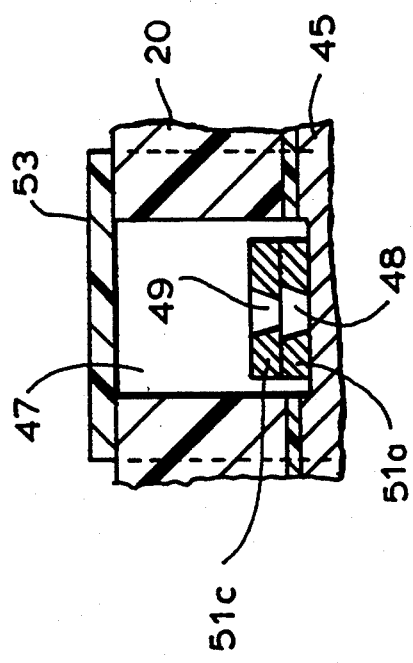
FIG. 5 is a fragmentary longitudinal sectional view of the catheter after crimping of the ring electrodes thereon.
Figure 6:
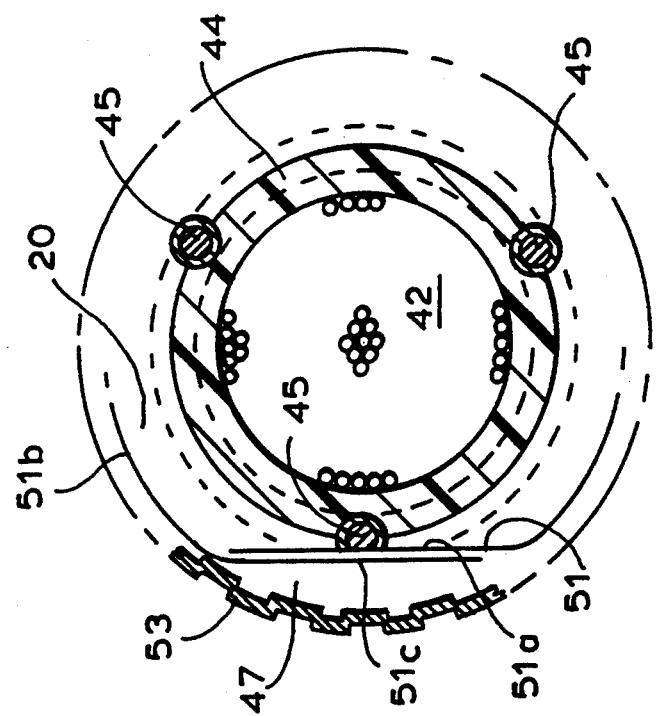
FIG. 6 is a transverse sectional view thereof to an enlarged scale, with the crimps being greatly exaggerated for expository purposes.
Figure 7:
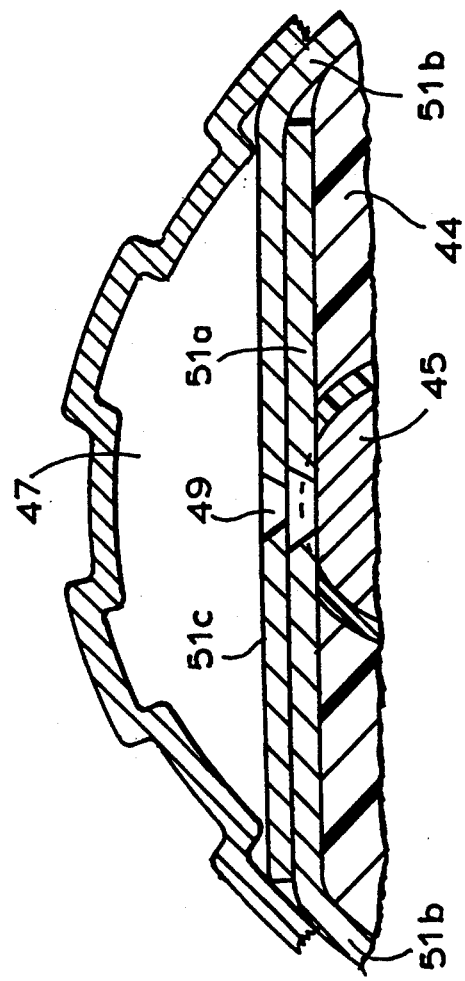
FIG. 7 is a transverse fragmentary sectional view thereof taken along the line 7—7 of FIG. 5, to a greatly enlarged scale, with the crimps being greatly exaggerated for expository purposes.

Referring now to FIGS. 5-7, to form the side electrodes 30a, a metal band or ring electrode 53, preferably formed of a biocompatible metal such as platinum or an alloy of platinum hardened with 10% iridium, is slid along the length of the hard layer 20 of tubing 12 to an appropriate location to cover one of the windows 47. The inner diameter of the ring electrode 53 is slightly larger than the outer diameter of the tubing 12 to enable the electrode 53 to slide over the hard layer 20 and over the top of the ribbon 51 at the location. The length of each ring electrode 53 (0.078 inch) is greater than the length of the window 47 it covers, so that the ring electrode 53 also extends over the adjacent surfaces of the hard layer 20. A crimping machine (not shown) is then employed to crimp the outer diameter of the ring electrode 53 down to the outer diameter of the tubing 12 (i.e., the hard layer 20). To this end, the crimping machine is provided with a circumferentially spaced plurality of crimping points (for example, 12 points equidistantly spaced about a circumference) which simultaneously crimp and collapse the band of electrode 53 to a preset diameter (e.g., 0.078 inch) so that the crimped or collapsed band retains its original circular configuration but with a reduced diameter. Preferably the crimping machine and the catheter workpiece are then relatively rotated (e.g., 15°) and crimping is performed a second time (thus making, for example, 24 equidistantly spaced crimp points), thereby to flatten out any high spots left by the first crimping. The length of each crimp is greater than the ribbon 51 so that each ring electrode 53 is crimped onto both ribbon 51 and the adjacent surfaces of the hard layer 20. The ribbon ends 51a, 51c and the ring electrode 53 are typically spaced apart, electrical contact between ribbon 51 and ring electrode 53 being effected through ribbon shank 51b.

It will be appreciated that, because the crimping operation squeezes the electrode band 53 flush with the tubing outer surface 21, an extremely smooth tubing/electrode interface is obtained without increasing the diameter of the tubing 12. Typically no subsequent hand smoothing of the exterior surface of the tubing at the tubing/electrode interface is required.

Accordingly, the present invention employs a crimping process which offers a significant cost advantage over conventional processes for producing a catheter with a flush outer surface by sharply reducing labor requirements and simplifying assembly. While crimping of the side electrodes 53 on the tubing 12 suffices to electrically and physically secure the electrode 53 to the ribbon 51 and hence to the associated exposed wound wire 45, excessive bending of the catheter during use may still result in a separation of elements enabling the electrode 53 to move relative to the ribbon 51 and hard layer 20. Accordingly, for extra security the ring electrode 53 is preferably finally welded to the ribbon 51. The welding may be performed using a conventional resistive welder with two electrodes which have been machined to the diameter of the electrode 53 so that the welder cannot damage the electrode under the pressure of the weld. A preferred resistive welder is available under the trade name Thin Line Welder (from Unitek Equipment Inc.).

As a highly-desirable by-product of the welding process, the heat generated thereby melts the hard layer 20 underneath the electrode 53, allowing it to reform and securely attach itself to the electrode 53. Accordingly, the electrode 53 adheres better to the hard layer 20 as well as the ribbon 51 and is less likely to separate therefrom during subsequent flexure of the catheter, thus enhancing reliability of the product.

The manufacturing process of the present invention is in all its aspects easy and inexpensive relative to the labor-intensive nature of most other manufacturing processes for producing an electrode-carrying catheter, while affording a product of enhanced reliability.

Referring now to FIG. 8, where the catheter 10 includes at least one end electrode 30b as one of the electrodes 30 thereof, the electrically conductive end electrode is preferably configured and dimensioned as a flexible cap, generally designated 60, disposed across the distal end 16 of the tubing 12 in order to close the same. The cap 60 may be formed of the same material as the ring electrodes or a different material. The cap 60 is of appreciable thickness and has a head 64 defining a recess 62 on its proximal surface and a proximally projecting circumferential band 66. As cap 60 is slipped over the distal end, the core extension 42a is received within cap recess 62, and the distal end of the hard layer 20 is received within the cap band 66. Referring now to FIG. 9, the head or cap distal end 64 is then crimped onto the core extension 42a, at 80, and the band or cap proximal end 66 is crimped onto and flush with the hard layer 20, at 82. This double crimping 80, 82, using a crimping machine as described hereinabove in connection with the crimping of the side electrodes 30a, securely joins the end electrode 30b with the core extension 42a and hard layer 20, neither a ribbon 51 nor a welding step being required.

As used herein, the terms "insulating", "insulative", "non-conducting" and "non-conductive" are synonyms.

To summarize, the present invention provides an electrode-carrying catheter of high reliability and low cost, the catheter being capable of mounting a large number of electrodes. There is reliable adhesive-free electrical contact between an electrode and any conductive wire extending from the proximal end to the electrode, with the electrode having a sufficiently large surface area for electrode functioning, and all exposed surfaces being biocompatible. The catheter is easily and inexpensively manufactured.

Now that the preferred embodiments of the present invention have been shown and described in detail, various modifications and improvements thereon will become readily apparent to those skilled in the art. Accordingly, the spirit and scope of the present invention is to be construed broadly and limited only by the appended claims, and not by the foregoing specification.

I claim:

1. An electrode-carrying catheter, comprising:
(A) elongate, flexible tubing defining a proximal end, a distal end, and an electrically insulative outer tubular layer intermediate said ends, said tubing including a flexible electrically conductive core of wire and a flexible non-conductive core-covering layer of plastic about said core;
(B) at least one electrically conductive ring electrode crimped on and flush with said outer tubular layer; and
(C) conducting means for conducting electrical signals between said proximal end and each of said at least one ring electrode, said conducting means including, intermediate said core and said outer tubular layer, a longitudinally-spaced plurality of flexible electrically conductive wires helically wound around and at least partially into said core-covering layer and insulated from one another at least by said core-covering layer and from the environment at least by said outer tubular layer, said outer tubular layer defining a removed section beneath a segment of each of said at least one ring electrode to enable electrical contact between a respective one of said wound wires and a respective one of said at least one ring electrode, said conducting means further including electrically conductive flexible flat means disposed intermediate each of said at least one ring electrode and said tubing for providing electrical communication between one of said at least one ring electrode and one of said wound wires, each of said flat means being electrically and physically joined to a respective one of said wound wires and wrapped about said outer tubular layer, each of at least one ring electrode being crimped onto a respective one of said flat means and said outer tubular layer.

2. The catheter of claim 1 wherein said flat means is joined to said wound wires by welding.

3. The catheter of claim 1, wherein said core-covering layer is softer than said outer tubular layer.

4. The catheter of claim 1, wherein said core-covering layer is over-extruded over said core, and said outer tubular layer is over-extruded over said wound wires and said core-covering layer.

5. The catheter of claim 1, wherein said flat means is a flat copper ribbon having a pair of opposed ends, said ribbon being electrically and physically joined at one end to a respective one of said wound wires, wrapped under tension completely about said outer tubular layer, and physically joined at the other end to itself.

6. The catheter of claim 1, wherein said core is a stranded and twisted configuration of annealed stainless steel wire having an appreciable torsional strength and a slow return after lateral bending.

7. The catheter of claim 1 wherein said core-covering layer and said outer tubular layer are formed of polyurethane.

8. The catheter of claim 1 wherein each of said wound wires is covered with electrical insulation, and said electrical insulation covering each wound wire defines a removed section beneath one of said at least one electrode.

9. The catheter of claim 1 wherein said at least one electrode are platinum with a minor proportion of iridium.

10. The catheter of claim 1 wherein each of said at least one ring electrode is crimped onto said flat means and said outer tubular layer at at least 24 crimp points.

11. The catheter of claim 1 wherein said at least one ring electrode crimped onto said flat means and said outer tubular layer are also welded to said flat means, and said outer tubular layer is reformed about said at least one ring electrode.

12. The catheter of claim 1 wherein said core has an extension projecting distally from said distal end, and an electrically conductive end electrode is crimped distally onto said core extension and is proximally crimped onto and radially flush with said outer tubular layer.

13. The catheter of claim 1 wherein, said wound wires include electrical insulation thereabout, and said outer tubular layer and said electrical insulation about said wound wires define said removal section.

14. An electrode-carrying catheter, comprising:
(A) elongate, flexible tubing defining a proximal end, a distal end, and an electrically insulative outer tubular layer intermediate said ends, said tubing including a flexible electrically conductive core of wire and a flexible non-conductive core-covering layer of plastic about said core, said core being a stranded and twisted configuration of annealed stainless steel wire having an appreciable torsional strength and a slow return after lateral bending, said core-covering layer being softer than said outer tubular layer and over-extruded over said core;
(B) at least one electrically conductive ring electrode crimped on and flush with said outer tubular layer; and
(C) conducting means for conducting electrical signals between said proximal end and each of said at least one ring electrode, said conducting means including, intermediate said core and said outer tubular layer, a longitudinally-spaced plurality of flexible electrically conductive wires helically wound around and at least partially into said core-covering layer and insulated from one another at least by said core-covering layer and insulated from one another at least by said core-covering layer and from the environment at least by said outer tubular layer, said outer tubular layer defining a removed section beneath a segment of each of said at least one ring electrode to enable electrical contact between a respective one of said wound wires and a respective one of said at least one ring electrode, said conducting means further including electrically conductive flexible flat means disposed intermediate each of said at least one ring electrode and said tubing for providing electrical communication between one of said at least one ring electrode and one of said wound wires, each of said flat means being a flat copper ribbon having a pair of opposed ends, said ribbon being electrically physically joined by welding at one end to a respective one of said wound wires, wrapped under tension completely about said outer tubular layer, and physically joined by welding at the other end to itself, each of said at least one ring electrode being crimped onto a respective one of said flat means and said outer tubular layer, said at least one ring electrode crimped onto said flat means and said outer tubular layer being also welded to said flat means, and said outer tubular layer being reformed about said at least one ring electrode, said outer tubular layer being over-extruded over said wound wires and said core-covering layer;

said core having an extension projecting distally from said distal, end and an electrically conductive and electrode being crimped distally onto said core extension and proximally crimped onto and radially flush with said outer tubular layer.

15. The catheter of claim 14 wherein, said wound wires include electrical insulation thereabout, and said outer tubular layer and said electrical insulation about said wound wires define said removed section.

* * * * *